(12) United States Patent
Bert et al.

(10) Patent No.: US 9,012,832 B2
(45) Date of Patent: Apr. 21, 2015

(54) METHOD AND DEVICE FOR CHECKING AN IRRADIATION PLANNING SYSTEM, AND IRRADIATION SYSTEM

(75) Inventors: Christoph Bert, Aschaffenburg (DE); Eike Rietzel, Weiterstadt (DE); Nami Saito, Darmstadt (DE)

(73) Assignees: Siemens Aktiengesellschaft, München (DE); GSI Helmholtzzentrum Für Schwerionenforschung GmbH, Darmstadt (DE)

( * ) Notice: Subject to any disclaimer, the term of this patent is extended or adjusted under 35 U.S.C. 154(b) by 152 days.

(21) Appl. No.: 13/498,903

(22) PCT Filed: Aug. 10, 2010

(86) PCT No.: PCT/EP2010/004956
§ 371 (c)(1),
(2), (4) Date: Jul. 12, 2012

(87) PCT Pub. No.: WO2011/038802
PCT Pub. Date: Apr. 7, 2011

(65) Prior Publication Data
US 2012/0273666 A1 Nov. 1, 2012

(30) Foreign Application Priority Data

Sep. 29, 2009 (DE) .......................... 10 2009 043 283

(51) Int. Cl.
*G01D 18/00* (2006.01)
*A61N 5/10* (2006.01)
(Continued)

(52) U.S. Cl.
CPC ..... *A61N 5/1048* (2013.01); *A61B 2017/00707* (2013.01); *A61N 2005/1087* (2013.01); *G21K 1/10* (2013.01)

(58) Field of Classification Search
USPC .................................... 250/252.1, 336.1, 393
See application file for complete search history.

(56) References Cited

U.S. PATENT DOCUMENTS 5,511,549 A * 4/1996 Legg et al. .................... 600/436
6,639,234 B1 * 10/2003 Badura et al. .............. 250/492.3
(Continued)

FOREIGN PATENT DOCUMENTS

WO WO 2004/103145 A2 12/2004

OTHER PUBLICATIONS

German Office Action dated Jun. 30, 2010 for corresponding German Patent Application No. DE 10 2009 043 283.3-54 with English translation.
(Continued)

*Primary Examiner* — David J Makiya
*Assistant Examiner* — Taeho Jo
(74) *Attorney, Agent, or Firm* — Lempia Summerfield Katz LLC

(57) ABSTRACT

The invention relates to a method for checking an irradiation installation in which a dose distribution is deposited in a target object by means of a treatment beam, said method comprising the following steps: an irradiation planning data record optimized for the irradiation of a moving target volume is provided; a movement signal that reproduces a movement of the target volume is provided; a phantom is irradiated, said phantom being formed for detecting a dose distribution deposited in the phantom during or after the irradiation, using the control parameters stored at the irradiation planning data record and the movement signal; a dose distribution deposited in the phantom is determined; a dose distribution to be expected is calculated on the basis of parameters that are related to the control of the irradiation installation during the irradiation; and the determined dose distribution deposited in the phantom is compared to the calculated dose distribution to be expected. The invention also relates to a corresponding device and an irradiation installation comprising such a device.

19 Claims, 5 Drawing Sheets

(51) Int. Cl.
*A61B 17/00* (2006.01)
*G21K 1/10* (2006.01)

(56) References Cited

U.S. PATENT DOCUMENTS

| | | | |
|---|---|---|---|
| 6,710,362 B2 | 3/2004 | Kraft et al. | |
| 6,799,068 B1* | 9/2004 | Hartmann et al. | 607/2 |
| 6,891,177 B1 | 5/2005 | Kraft et al. | |
| 7,371,007 B2* | 5/2008 | Nilsson | 378/207 |
| 2002/0077545 A1* | 6/2002 | Takahashi et al. | 600/424 |
| 2005/0185758 A1* | 8/2005 | Bruder et al. | 378/65 |
| 2006/0033042 A1* | 2/2006 | Groezinger et al. | 250/492.1 |
| 2006/0203967 A1* | 9/2006 | Nilsson | 378/207 |
| 2008/0170663 A1* | 7/2008 | Urano et al. | 378/65 |
| 2008/0298540 A1* | 12/2008 | Serban et al. | 378/18 |
| 2009/0095921 A1 | 4/2009 | Bert et al. | |
| 2009/0116616 A1* | 5/2009 | Lu et al. | 378/65 |
| 2009/0304154 A1* | 12/2009 | Lomax et al. | 378/65 |
| 2010/0108903 A1* | 5/2010 | Bert et al. | 250/396 R |
| 2010/0301235 A1* | 12/2010 | Bert et al. | 250/492.3 |
| 2010/0327188 A1* | 12/2010 | Bert et al. | 250/492.3 |
| 2011/0309255 A1* | 12/2011 | Bert et al. | 250/363.03 |

OTHER PUBLICATIONS

European Office Action dated Aug. 5, 2013 for corresponding European Patent Application No. 10 748 049.3-1652 with English translation.
PCT Written Opinion of the International Searching Authority dated Mar. 29, 2012 for corresponding PCT/EP2010/004956.
Y. Vinogradskiy et al., "Verification of four-dimensional photon dose calculations," Medical Physics, vol. 36, No. 8, pp. 3438-3447, 2009.
C. Bert et al., "4D Treatment Planning for Scanned Ion Beams," Radiation Oncology, 2:24, pp. 1-10, 2007.
S. O. Grözinger et al., "Motion Compensation with a Scanned Ion Beam: a Technical Feasibility Study," Radiation Oncology, 3:34, pp. 1-7, 2008.
L. Wang et al., "Experimental Verification of a CT-Based Monte Carlo Dose-Calculation Method in Heterogeneous Phantoms," Medical Physics, vol. 26, No. 12, pp. 2626-2634, 1999.
T. Moser et al., "Detection of Respiratory Motion in Fluoroscopic Images for Adaptive Radiotherapy," Phys. Med. Biol., 53, pp. 3129-3145, 2008.
V. F. Physik et al., "Bestrahlungsplanung für bewegte Zielvolumina in der Tumortherapie mit gescanntem Kohlenstoffstrahl," pp. 1-7, 2006.
Q. Li et al., "Online Compensation for Target Motion with Scanned Particle Beams: Simulation Environment," Physics in Medicine and Biology, 49, pp. 3029-3046, 2004.
R. Lüchtenborg et al., "On-line Compensation of Dose Changes Introduced by Tumor Motion During Scanned Particle Therapy," pp. 449-452, 2009.
C. Bert et al., "Quantification of Interplay Effects of Scanned Particle Beams and Moving Targets," Phys. Med. Biol. 53, pp. 2253-2265, 2008.
S. Minohara et al., "Respiratory Gated Irradiation System for Heavy-Ion Radiotherapy," International Journal of Radiation: Oncology Biology Physics, vol. 47, No. 4, pp. 1097-1103, 2000.

* cited by examiner

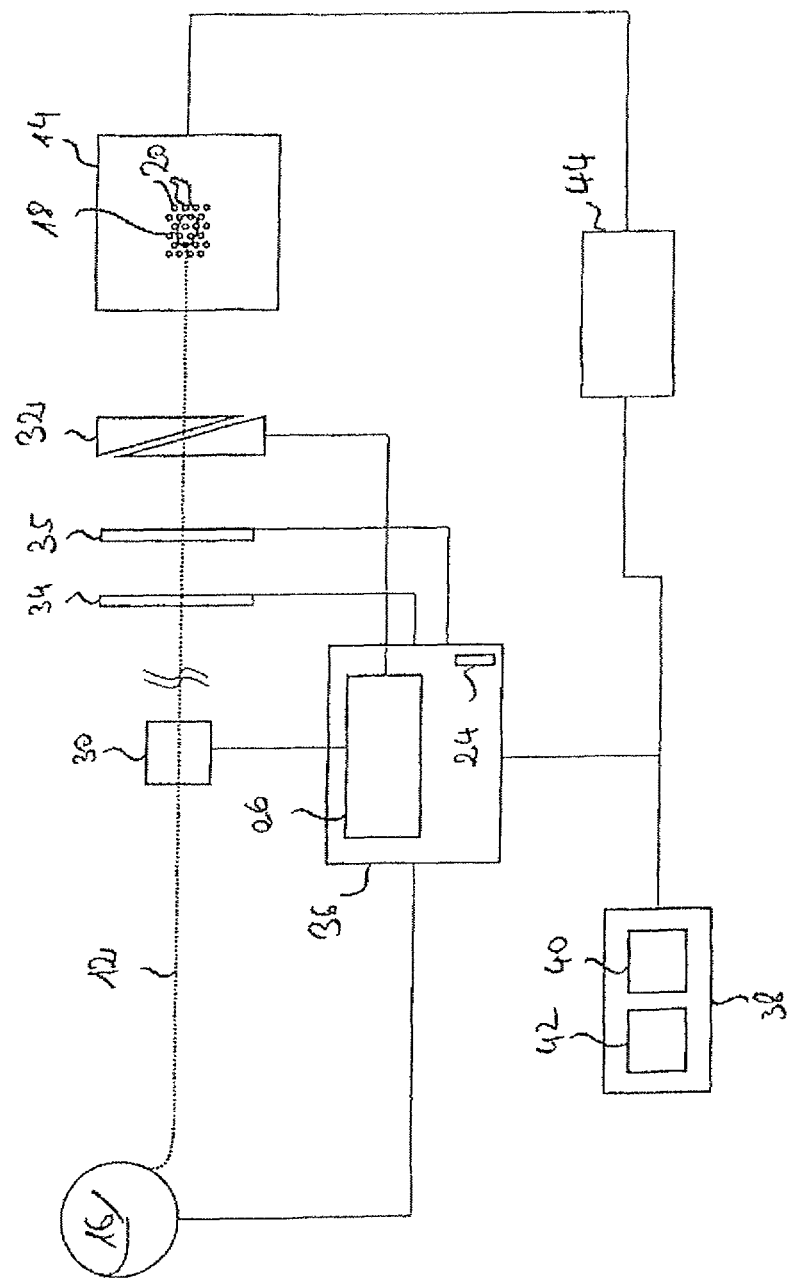

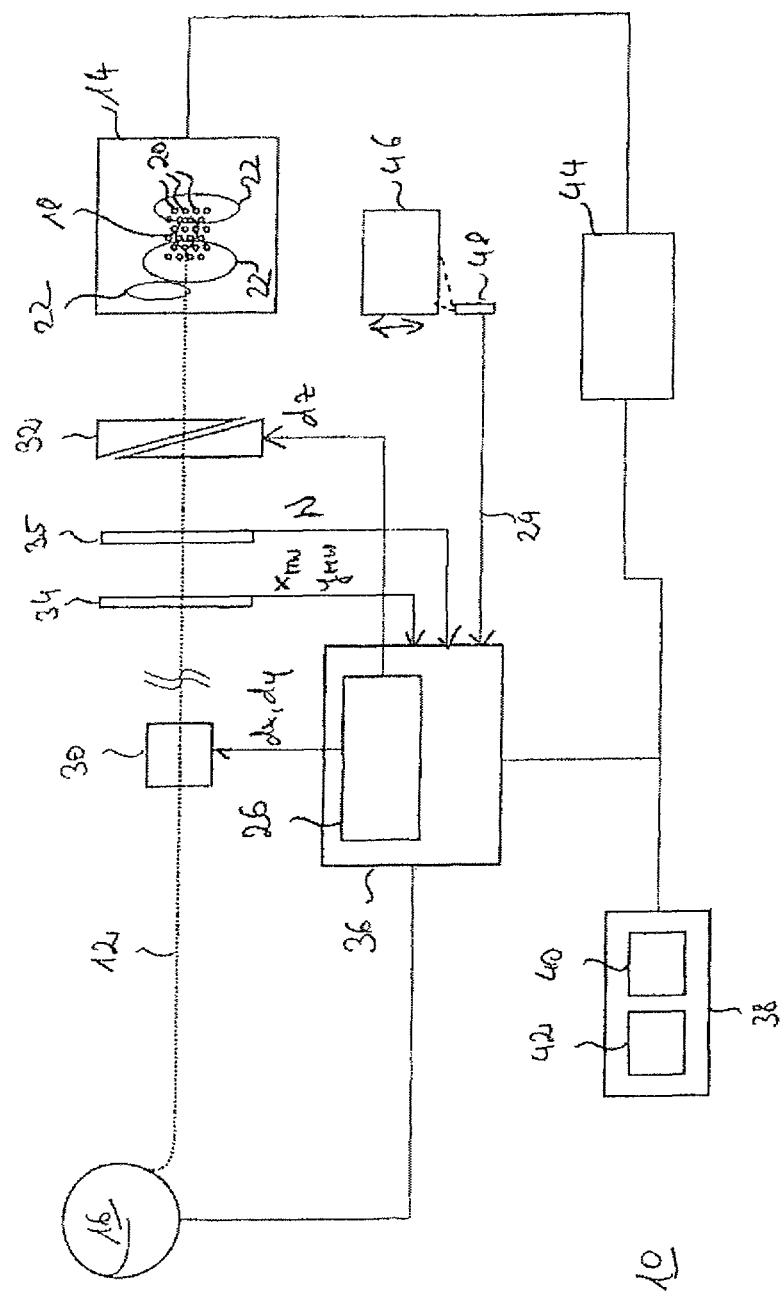

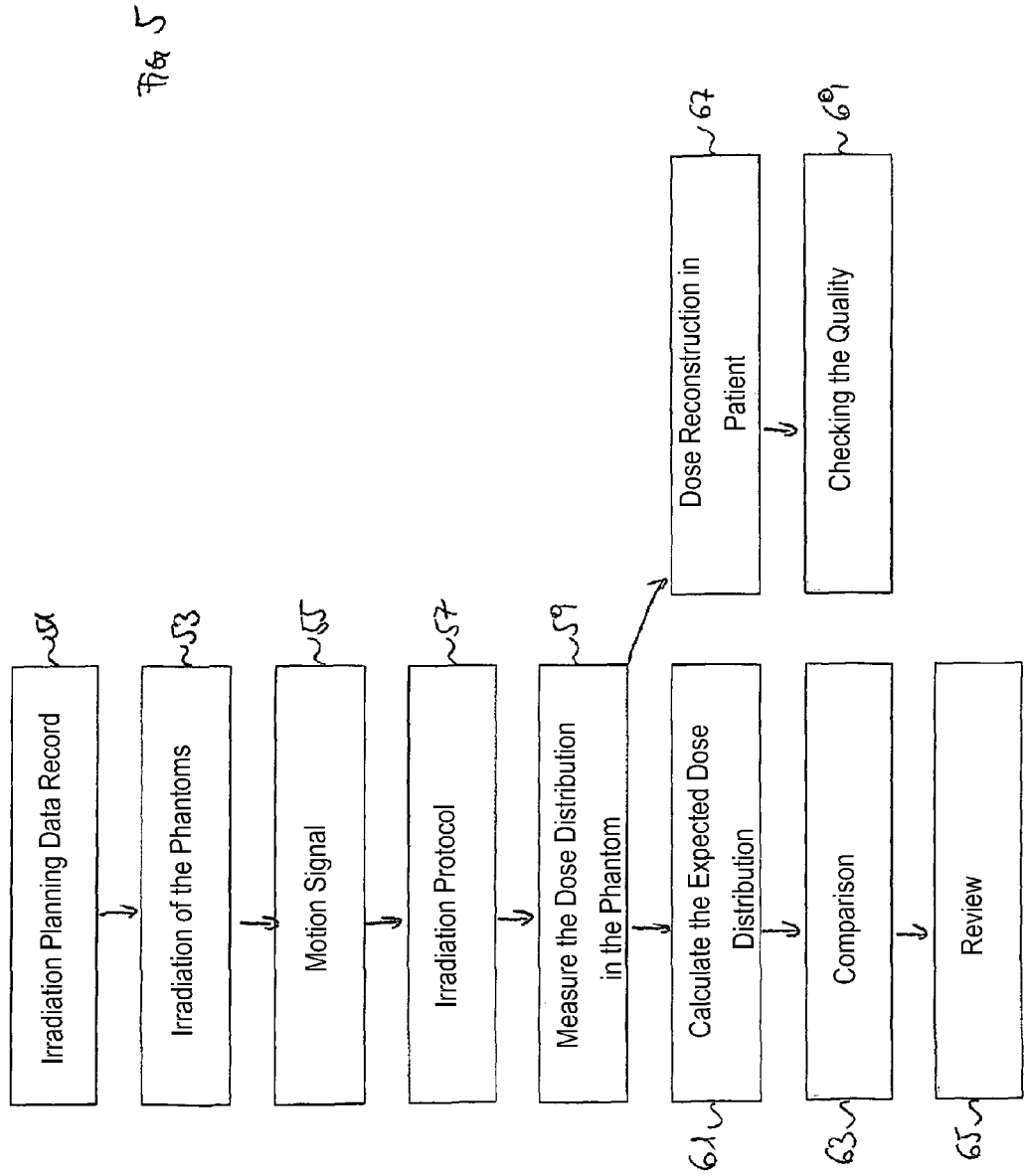

METHOD AND DEVICE FOR CHECKING AN IRRADIATION PLANNING SYSTEM, AND IRRADIATION SYSTEM

The present patent document is a §371 nationalization of PCT Application Serial Number PCT/EP2010/004956, filed Aug. 12, 2010, designating the United States, which is hereby incorporated by reference. This patent document also claims the benefit of DE 10 2009 043 283.3, filed on Sep. 29, 2009, which is also hereby incorporated by reference.

BACKGROUND

The present embodiments relate to a method and an apparatus for monitoring an irradiation system.

Methods and apparatus for monitoring an irradiation system may be used, for example, prior to a planned irradiation for evaluating whether the system is functioning correctly.

Particle therapy is an established method for treating tissue (e.g., for treating tumor diseases). However, irradiation methods of the kind used in particle therapy are also used in nontherapeutic fields. Examples include research work (e.g., for product development), in the context of particle therapy done on non-living phantoms or bodies, and the irradiation of materials.

In such fields, charged particles such as protons or carbon ions or other ions are accelerated to high energy levels, shaped into a particle beam, and guided to one or more irradiation chambers via a high-energy beam transportation system. In the irradiation chamber, the target volume to be irradiated is irradiated with the particle beam.

It may happen that the target volume to be irradiated moves. For example, when a patient is being irradiated, a respiratory motion may cause the tumor that is to be irradiated to move.

One known way of compensating for the motion of the target volume is irradiation methods that are known by the terms "rescanning," "gating," and "tracking." "Rescanning" may be that the beam is applied as planned multiple times, so that incorrect doses in the individual scans are averaged. "Gating" may be that the beam is applied only within fixed time slots of the motion, so that the influence of the motion is lessened or even excluded entirely. "Tracking" may be that the beam, with which the target volume is being irradiated, tracks the motion of the target volume. If the beam is a particle beam, this may be attained, for example, by deflecting the beam using magnet systems, such that a course of the motion of the target volume is tracked. Optionally, the beam may also be varied in energy to adapt the penetration depth of the beam to the motion of the target volume. Tracking may also be done in irradiation with photons. This may be done, for example, by modifying the collimator that limits the beam, the collimator opening being adapted to the motion of the target volume.

Methods and apparatuses, with which motion tracking of the beam may be achieved, are known from U.S. Pat. No. 6,891,177 B1 and U.S. Pat. No. 6,710,362 B2, and US patent application 2006/0033042 A1.

These compensatory methods may be employed in the context of particle therapy in a scanning process, in which a plurality of spatially narrow irradiation doses are deposited successively at various sites in the target volume. In other words, these compensatory methods may be employed in the context of particle therapy in a scanning process, in which the particle beam sweeps in a scanning fashion over the target volume.

SUMMARY AND DESCRIPTION

The present embodiments may obviate one or more of the drawbacks or limitations in the related art. For example, a method for monitoring an irradiation system and/or for monitoring an irradiation planning that permits safe operation of the irradiation system even when target volumes that are in motion are being irradiated, is provided.

Both the above description of the individual features and the description that follows relate both to the apparatus and the method, without this being mentioned explicitly and in detail in every case; the individual features disclosed may also be provided in other combinations besides those shown.

The method according to the present embodiments for monitoring an irradiation system (e.g., a particle therapy system), in which with a treatment beam, a dose distribution may be deposited in a target object, includes the following acts: furnishing an irradiation planning data set that is designed or optimized for irradiating a moving target volume; furnishing a motion signal that simulates a motion of the target volume; irradiating a phantom that is embodied for detecting a dose distribution deposited in the phantom during or after the irradiation; the phantom being irradiated by using the control parameters stored in the irradiation planning data set and the motion signal; ascertaining a dose distribution deposited in the phantom; calculating an expected dose distribution on the basis of parameters that are related to the control of the irradiation system during the irradiation; comparing the ascertained dose distribution deposited in the phantom with the calculated expected dose distribution.

Quality assurance for irradiating a target volume that is in motion is substantially more difficult to achieve than in irradiating a static target volume, since with the motion, there is one additional parameter that may lead to mistakes during the irradiation. For example, the motion of the target volume is a factor that may not be determined until during the irradiation and may not be precisely predicted beforehand.

In one embodiment, in the quality monitoring, a phantom is irradiated, so that a dose distribution in accordance with an irradiation planning data set and a furnished motion signal is deposited in the phantom.

A calculation of the dose distribution to be expected in the phantom is made. For this calculation, data that are used for controlling the irradiation system during the irradiation (e.g., not only parameters that are stored in the irradiation planning data set and may be used directly or indirectly for controlling the irradiation system, but also data that are logged during the actual irradiation and characterize the course of the irradiation and the actual properties of the beam during the irradiation) may be used. The data also include the recorded motion trajectory, correlated chronologically with the irradiation.

The calculated expected dose distribution is compared with the dose distribution that is measured or ascertained from the phantom. By the comparison of the expected dose distribution with the dose distribution actually applied in the phantom and ascertained from the phantom, whether the irradiation is being performed correctly may be ascertained, even if the irradition method compensates for the motion of a target volume. Calculating the dose distribution in a particle therapy system includes, for example, the calculation of the penetration depth of the particle beam in the target object (e.g., in the target volume). The calculation of the dose distribution in the particle therapy system may also include the calculation of the penetration depth of the particle beam in regions surrounding the target volume. If the calculated expected dose distribution corresponds to or approximately matches the dose distribution ascertained, good function of the irradiation apparatus may be confirmed, and the irradiation plan may thus be validated.

The irradiation of the phantom takes place such that a motion compensation is done based on the control parameters stored in the irradiation planning data set (e.g., in combination with the motion signal). The phantom is irradiated as if the phantom were moving in accordance with the motion signal. The motion compensation system of the overall system controls the irradiation of the overall system as if a target volume were moving in accordance with the motion signal. The motion compensation system of the overall system may be embodied in various ways and may, for example, implement a tracking method and/or a gating method and/or a rescanning method. The motion compensation system consequently minimizes the dosimetric influence of the motion of a target volume.

The phantom is embodied such that during or after the irradiation of the phantom, the dose deposited in the phantom or more precisely, the spatial distribution of the dose deposited in the phantom, may be ascertained or measured. In a simple case, the phantom may be a two-dimensional film that is blackened upon being irradiated with the treatment beam. By evaluation of the film after the irradiation, the dose distribution may be evaluated two-dimensionally and thus ascertained. The blackening thus ascertained may be compared with the dose distribution or film blackening to be expected. In one embodiment, however, the phantom is constituted three-dimensionally to enable ascertaining the dose distribution three-dimensionally. For example, many dosage measurement chambers may be integrated with a three-dimensional body. The dose distribution deposited in the phantom is measured by evaluating the signals generated in the dosage measurement chambers. A phantom that includes biological cellular material may also be used, so that the dose distribution or the influence of the irradiation may be obtained by evaluating the irradiated cellular material.

The phantom may be constituted homogeneously, or more precisely, the material, with which the dosage measurement chambers are integrated, is homogeneous. The material may also be nonhomogeneous with various regions that show a different penetration depth for a particle beam. Thus, the constitution of a human body (e.g., with various organs and tissues) may be simulated (e.g., anthropomorphic phantom).

The irradiation planning data set may be a three- and, for example, a four-dimensional irradiation planning data set. The four-dimensional irradiation planning data set may be that the irradiation planning data set takes into account the dimension of time and the motion of the target volume. This kind of irradiation planning data set may be based on a four-dimensional imaging data set that depicts the motion of the target volume. The dose distribution in the target volume and the corresponding adaptation may be planned on the basis of the four-dimensional imaging data set, so that the desired irradiation may be provided despite the motion of the target volume. One example of such a four-dimensional irradiation planning data set is disclosed in US patent application 2009/0095921 A1, which describes a four-dimensional irradiation planning data set for a scanning process in a particle therapy system, in which the particle beam tracks the motion of the target volume. The irradiation planning data set includes the dose distribution and the requisite beam parameters for a reference phase. The irradiation planning data set also includes compensatory parameters for other phases of motion, with which the beam parameters of the reference phase are varied to provide the correct dose deposition in the target volume despite the motion of the target volume. A four-dimensional irradiation planning data set, together with the motion signal during the irradiation, may control the irradiation such that the desired dose distribution in the target volume is attained despite the motion of the target volume.

The four-dimensional irradiation planning data set may be created on an irradiation planning device and loaded into a control device of the irradiation system. Based on the parameters stored in the irradiation planning data set, the control device may control the beam application and, for example, the motion compensation in the beam application. As the motion compensation, tracking of the motion of the beam, for example, may be done.

The motion tracking during the irradiation is performed based on a motion signal. Since a phantom, and not the target volume, for which the irradiation planning was done, is irradiated, a motion signal that simulates the motion of the target volume is furnished. Therefore, the motion signal merely reflects a possible signal that may occur during an irradiation of the target volume. The motion of the target volume is accordingly simulated by the motion signal.

The motion signal may, for example, be generated by providing that a motion detection device (e.g., an external sensor) that monitors the motion during an irradiation of the target volume is stimulated by a moving physical object. If the external sensor is an optical sensor, for example, with which the motion of a marker applied to a patient may be tracked, then using a movement device, a marker may be moved. Motion of the marker is detected by the sensor in order to generate the motion signal. This embodiment has the advantage that the motion monitoring device is likewise monitored with the external sensor. In another embodiment, the motion signal may be generated internally in a computer unit, so that the motion signal is a purely virtual motion signal that does not correlate with a physically moving object.

The phantom may, for example, be a moving phantom. The motion may be effected by a movement device provided for the phantom. The motion of the target volume to be irradiated may be simulated by the motion of the phantom. For generating the motion signal, the motion detection device may monitor the motion of the phantom. The motion of the phantom is advantageous whenever in the irradiation, a gating or rescanning method is used as a method of compensating for a motion. The motion may also be designed such that the motion does not correspond to the motion signal. The advantage of this is that as a result, the pattern of the dose distribution may be varied. A dose distribution originally planned to be homogeneous may, using the different motion patterns, generate a nonhomogeneous dose distribution in the phantom. This may sometimes also be easier to evaluate.

The movement device may be controlled such that critical motion trajectories are simulated (e.g., motion trajectories that put a maximum load on the motion compensation system). The motion trajectories may, for example, simulate the abrupt change in a motion status (e.g., from coughing), a constant drift in the baseline of the movement system, or a motion with a scope that exceeds the original irradiation planning. This may cause the scope of look-up tables, for example, in which compensatory parameters are stored, or margins of safety, to be exceeded. In such motion trajectories, the interlock system of the overall system, which interrupts an irradiation in such critical cases, may also be monitored.

In order for the quality of the motion compensation to be monitored, however, the phantom may not be a moving phantom. For example, the phantom may have a different motion pattern from what is reflected by the simulated motion signal. Thus, the motion pattern of the phantom may differ from a motion phantom having motion that is detected for simulating the motion signal. A phantom with that kind of motion pattern is employed in combination with a tracking method, in which the particle beam, controlled by the motion signal, is deflected in the local position. Advantageously, the phantom may even be a static phantom, even though motion compensation is being monitored in the method.

This embodiment is based on the fact that interference effects occur if a target volume moves during the irradiation and if the beam does not track the motion. The result at some points in the target volume may be an unwanted overdose or underdose relative to the planned dose distribution. However, tracking that is employed for the sake of avoiding interference effects is what leads to similar "inverse" interference effects if a phantom that is subject to a different motion pattern from that reflected in the motion signal is being irradiated.

The combination of a phantom, which has a different motion pattern from that indicated by the motion signal, with the tracking method leads to a dose distribution in the phantom that has a characteristic distribution pattern. For example, an originally planned homogeneous dose distribution generates a nonhomogeneous dose distribution in the phantom. This nonhomogeneous dose distribution may be compared with an expected nonhomogeneous dose distribution that is calculated from data that are in relation to the motion compensation during the irradiation.

This embodiment is based on the nonhomogeneous dose distribution being sensitive to errors in the motion compensation system in the irradiation and deviations being more easily detected than with a homogeneous dose distribution. The comparison of the ascertained dose distribution pattern with the expected nonhomogeneous dose distribution pattern is efficient for finding any errors in the irradiation system and in the motion compensation system.

The parameters used for calculating the expected dose distribution may include control parameters that are data stored in the irradiation planning data set, and the motion signal. These parameters are sufficient to calculate the expected dose distribution. On the basis of these parameters, a sequence, for example, that predicts the irradiation course and indicates when and where which partial dose is to be deposited may be ascertained (e.g., when the particle beam is located at what location, so that with the sequence of the specific motion trajectory and the specific irradiation times, the entire dose distribution to be expected may be calculated).

Advantageously, however, data that characterize the property of the applied treatment beam in the course of time during the irradiation enter into the calculation. These data may be logged, for example, in the course of the irradiation. The data, for example, may be the actual position of the beam (x, y, z), actual compensation parameters (dx, dy, dz), the actual number (N) of particles in the treatment beam, and possible compensation parameters (dN) (e.g., the actual number of particles applied per target point and/or an intensity of the treatment beam), so that from the data characterizing the actual course of the irradiation, the expected dose distribution may be ascertained. This embodiment has the advantage that the embodiment is not, like the prediction of the irradiation course, based on assumptions that may not fit the reality. With this embodiment, uncertainties and limits of the motion compensation system of the overall system may also be ascertained in the form in which the uncertainties and limits are present.

The calculation of the expected dose distribution also takes into account the constitution of the phantom, since the constitution of the phantom (e.g., with particle beams) is connected to the penetration depth of a beam. For example, in a phantom with a nonhomogeneous constitution, a different dose distribution is to be expected from that with a phantom with a homogeneous constitution.

In one embodiment, the parameters are used to correlate the dose distribution with an imaging data set that is the basis for the irradiation planning data set. The dose distribution may be reconstituted in the imaging data set (e.g., in a four-dimensional computer program). For example, whether the expected dose distribution is optimally adapted to the anatomy of a patient and what effect an irradiation with motion compensation would have in the context of the patient's anatomy may be checked. For example, whether the distal edge of the target volume would be adequately irradiated or whether any organs at risk would be adequately spared may be checked.

The apparatus according to the embodiments for monitoring an irradiation system (e.g., a particle therapy system), in which with a treatment beam, a dose distribution may be deposited in a target object, includes: a device for furnishing an irradiation planning data set (e.g., an irradiation planning device or an interface for loading an irradiation plan) that is optimized for irradiating a moving target volume; a device for furnishing a motion signal that simulates a motion of the target volume (e.g., a motion detection device or a computer unit), with which a motion signal may be generated; a phantom that is embodied for detecting a dose distribution deposited in the phantom during or after the irradiation; a computer device that is embodied for calculating an expected dose distribution in the phantom that has been attained by the irradiation with parameters of the irradiation planning data set (e.g., on the basis of parameters that are related to the control of the irradiation system during the irradiation), and for comparing an ascertained dose distribution deposited in the phantom with the calculated expected dose distribution.

The outcome of the comparison may be presented to a user who may then decide which provisions to make. Examples are maintenance of the overall system or adaptation or modification of the irradiation planning data set. For example, a signal may be output if the comparison finds a deviation that is above a threshold value.

The irradiation system of the present embodiments (e.g., a particle therapy system) has such an apparatus for monitoring an irradiation system. The control device of the irradiation system for controlling an irradiation includes a motion compensation system, so that with the irradiation system, even moving target volumes may be irradiated.

BRIEF DESCRIPTION OF THE DRAWINGS

FIGS. 2, 3 and 4 show a schematic layout of a particle therapy system, in which the quality monitoring of embodiments of an irradiation method with motion compensation is performed; and FIG. 5 is a flow chart showing various exemplary method acts that may be performed in one embodiment of a method for monitoring an irradiation planning.

DETAILED DESCRIPTION OF THE DRAWINGS

Figure 1:
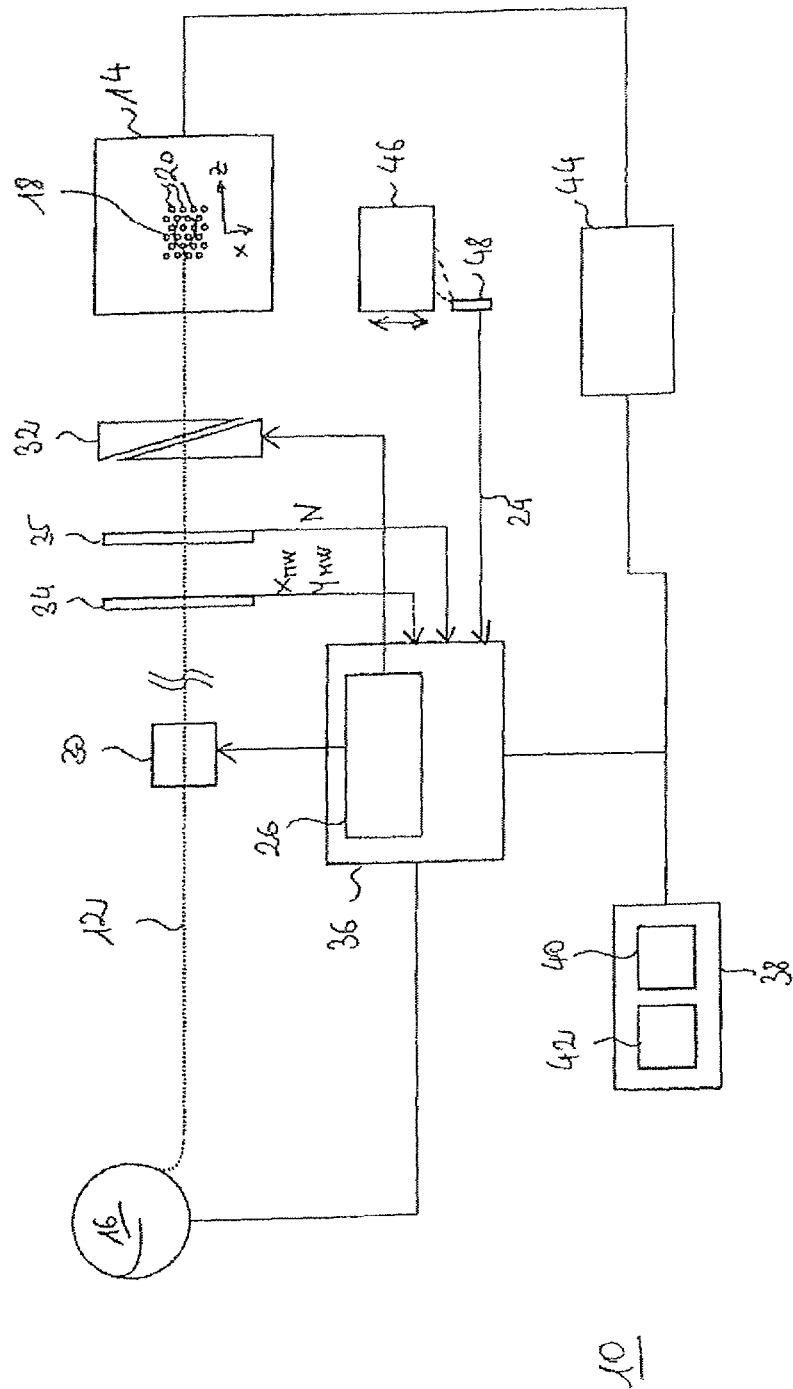
FIG. 1 shows a schematic layout of a particle therapy system, in which the quality monitoring of one embodiment of an irradiation method with motion compensation is performed.

FIG. 1, in a schematic illustration, shows a layout of a particle therapy system 10. The particle therapy system 10 is used for irradiating a body placed on a positioning device with a beam of particles (e.g., a particle beam 12). As a target volume, a patient's tissue diseased with tumor may, for example, be irradiated with the particle beam 12. However, for quality monitoring for an irradiation method, in which motion compensation is employed in order to adapt the application of a dose distribution to a motion of the target volume, a phantom 14 is irradiated.

In the phantom 14 to be irradiated, the dose distribution is deposited in a target region 18 that, for example, corresponds to the target volume that is defined in an irradiation planning data set. A plurality of detectors 20 is distributed in the phantom 14 for detecting the dose distribution with spatial resolution. After or during the irradiation of the phantom 14, the actually deposited dose distribution may be ascertained with spatial resolution.

The particle therapy system 10 may have an accelerator unit 16 (e.g., a synchrotron, cyclotron, or other accelerator) that furnishes the particle beam 12 with requisite energy for the irradiation. As the particles, protons, pions, helium ions, carbon ions, or ions of other elements are used. In one embodiment, the particle beam 12 has a beam diameter of 3 to 10 mm. For example, the particle beam 12 sweeps in a scanning pattern over the target volume.

As the scanning method, a raster scanning method, in which the particle beam 12 is deflected successively to various target points in the phantom 14 and in which the particle beam 12 applies a partial dose stored in memory in the irradiation planning data set at each of the various target points. The particle beam 12 is deflected from target point to target point. In one embodiment, the particle beam 12 is not shut off between the individual target points. Spot scanning methods with a shutoff of the particle beam 12 between the individual target points or other scanning methods such as continuous scanning may also be used for irradiating the target region with the particle beam 12.

The particle beam 12 may be laterally deflected using a system of scanning magnets 30. In other words, the particle beam 12 is deflected in a position perpendicular to a beam course direction (e.g., the x and y directions). An energy modulation device 32 may also be provided. The energy of the particle beam 12 may be quickly changed with the energy modulation device 32, so that a penetration depth of the particle beam 12 and thus a site of the Bragg peak may be varied in the z direction.

A tracking method may thus be implemented. This provides that in the irradiation of the target volume, an actual site of the particle beam (x, y, z) is varied by an amount of correction values (dx, dy, dz). If needed, the number (N) of particles to be applied per target point is varied by correction values (dN). The correction values (dN) are controlled on the basis of a motion signal and compensate for a deviation from an ideal position that is due to a moving target volume.

The overall system has site detectors 34 and intensity detectors 35 for monitoring beam parameters (e.g., an actual lateral deflection ($x_{MW}$, $y_{MW}$) and a number (N) of particles actually applied).

The irradiation system 10 and, for example, the irradiation procedure are controlled by a control device 36. The control device 36, with the aid of which an irradiation planning data set 40 may be loaded and implemented for the specific control of the irradiation system 10, includes a motion compensation device that is embodied as a beam tracking unit 26. The beam tracking unit 26 sends control parameters to the scanning magnets 30 for adapting (dx, dy) a lateral site of the particle beam 12 (x, y) to a displacement of the target volume. The beam tracking unit 26 also sends the control parameters to the energy modulation device 32 for adapting (dz) a longitudinal site (z) of the Bragg peak of the particle beam 12. In one embodiment, the number (N) of particles to be applied at a target point is also adapted (dN). The compensation parameters are ascertained with the aid of a four-dimensional irradiation planning data set 40 and with the aid of a motion signal 24 during the irradiation.

The control device 36 logs data recorded with the detectors 34, 35, so that from the logged data, when the particle beam 12 was applied, at which site the particle beam 12 was applied, and how intensively the particle beam 12 was applied may be reconstructed.

In one embodiment, the control is done based on an irradiation plan (e.g., on an irradiation planning data set 40 that is ascertained and furnished with the aid of an irradiation planning device 38). The irradiation planning data set 40 shown in FIG. 1 was created for a patient (not shown) with a target volume to be irradiated that moves. The irradiation planning data set 40 takes this motion into account and may therefore be referred to as a four-dimensional irradiation planning data set 40. The irradiation planning data set 40 may be created on the basis of a four-dimensional computed tomography scan 42.

The particle therapy system 10 has a computer unit 44, with which the dose distribution detected by irradiating the phantom 14 may be compared with an expected dose distribution that is calculated from data of the motion signal 24, data of the four-dimensional irradiation planning data set 40, and data of the logged beam parameters. For the sake of simplicity, the computer unit 44 is shown in FIG. 1 as a separate unit. However, the functionality performed by the computer unit 44 may also be implemented in already existing components (e.g., in control components of a particle therapy system 10).

If there is too great a deviation of the dose distribution ascertained from the phantom 14 from the calculated dose distribution, a signal is output that indicates to a user that the irradiation system 10 and/or the irradiation planning 40 is to be varied before the irradiation planning data set 40 may be implemented in a patient. In one embodiment, the correction may be performed automatically. However, a user may create a new dose distribution and/or assess the new distribution manually.

In FIG. 1, the phantom 14 is embodied in static form. The motion is simulated by moving a separately provided motion phantom 46 using a movement device (not shown) so that a motion detection device 48 may detect a motion and generate a motion signal 24.

With the aid of the motion signal 24, the control device 36 and the beam tracking unit 26 perform tracking of the particle beam 12 as if the phantom 14 to be irradiated were to move as indicated by the motion signal 24.

Because of the motion tracking of the particle beam 12, the dose distribution deposited in the static phantom 14 has a characteristic dose distribution pattern. This dose distribution pattern is sensitive to deviations from a planned irradiation. By comparison of the measured dose distribution pattern with the calculated dose distribution pattern, inaccuracies in the irradiation may be detected sensitively.

Figure 2:
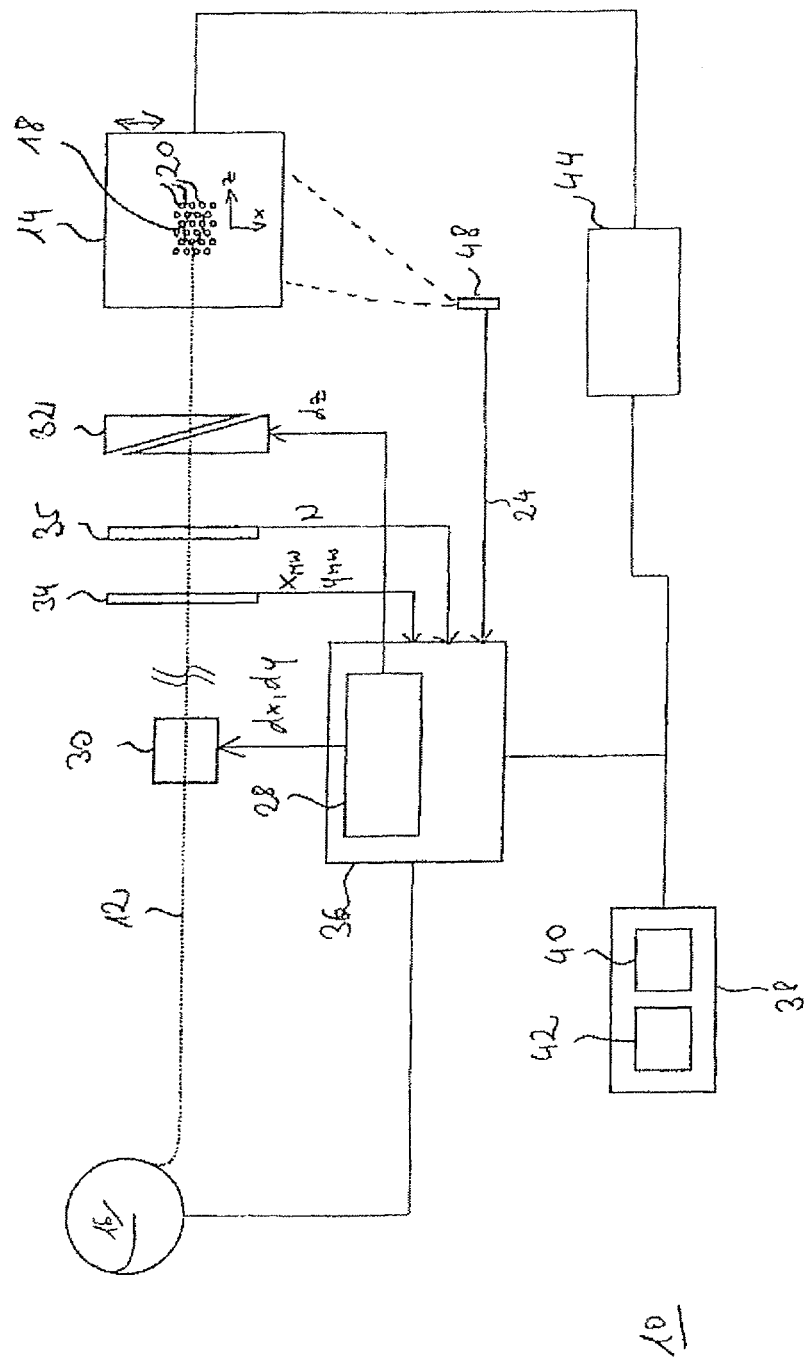

FIG. 2 differs from the particle therapy system 10 shown in FIG. 1 in that the phantom 14 is moved using a movement device not shown. The motion of the phantom 14 is detected with the motion detection device 48, and the control device 36 controls the irradiation procedure based on the detected motion. The motion compensation device 28 is embodied in FIG. 2 such that the motion compensation is performed with the aid of a gating method or a rescanning method. The gating method is based on an adaptation of the irradiation (e.g., turning the irradiation on and off) on the basis of the motion signal 24 detected. Depending on the embodiment, the rescanning method may also be based on an adaptation of the irradiation (e.g., the individual rescanning sweeps) on the basis of the motion signal detected.

FIG. 3 differs from the particle therapy system 10 shown in FIG. 1 in that in the quality monitoring, the motion detection device is dispensed with. The motion signal 24 is, for example, generated internally in the control device 36 and is a purely virtual signal 24 that, for example, simulates the movement of the center of gravity of a target volume. This has the disadvantage that any error sources that may be dictated by the motion compensation device are not detected. It has the advantage, however, that no motion phantom or separate measuring instrument for generating the motion signal 24 is needed.

FIG. 4 differs from the embodiment of FIG. 1 in that the phantom 14 shown has a plurality of different regions 22, in which the particle beam 12 has different penetration depths. With this kind of phantom 14, the anatomy of a patient may, for example, be simulated to make it possible to monitor more-realistic irradiation scenarios. In calculating the dose distribution, the various penetration depths in the phantom 14 are taken into account. This may be done, for example, using a CT scan of the phantom 14, on the basis of which the reach of the particle beam 12 in the phantom 14 may be determined.

FIG. 5 shows a schematic overview of the various method acts that may be performed in one embodiment of the method.

An irradiation planning data set based on a 4D CT of a patient is furnished (act 41).

This irradiation plan, however, is first used to irradiate a phantom (act 53) based on a furnished simulated motion signal (act 55).

During the irradiation, the characteristic beam parameters that characterize the irradiation (e.g., the course of the site over time, and/or the deflection of the particle beam, and/or other properties of the particle beam such as the intensity, the actual number of particles, or the focus) are recorded, and an irradiation protocol is created (act 57).

The dose distribution that has been applied in the phantom in the irradiation is measured or ascertained (act 59).

The expected dose distribution in the phantom that would be performed by the irradiation on the basis of parameters of the irradiation planning data set, and therefore based on the irradiation planning data set, on the motion signal used during the irradiation and on the measurement and control data logged during the irradiation, is calculated (act 61). The calculation of the dose distribution may incorporate an image of the phantom (e.g., a CT scan of the phantom).

The calculated dose distribution to be expected is compared with the actually ascertained and measured dose distribution of the phantom (act 63). As a result, monitoring of the irradiation system or particle therapy system and/or of the irradiation planning data set may be done (act 65).

In an optional act, using the irradiation planning data set, the motion signal used during the irradiation and the measurement and control data logged during the irradiation, a dose distribution may be calculated in a CT scan of the patient (act 67) (e.g., in the (chronologically resolved) CT scan that was the basis for the irradiation planning data set).

Using the calculation, how, in an actual irradiation, the dose distribution would affect a patient may be determined. The quality of a planned irradiation may be monitored with regard to the anatomical conditions actually present (act 69).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for monitoring an irradiation planning, the method comprising:
providing an irradiation planning data set that is created for irradiating a moving target volume;
providing a motion signal that simulates a motion of the target volume;
irradiating, using an irradiation system, a phantom with an ion particle beam using control parameters stored in the irradiation planning data set and the motion signal, the phantom being configured for detecting a dose distribution deposited in the phantom during or after the irradiation;
ascertaining the dose distribution deposited in the phantom;
calculating an expected dose distribution on the basis of parameters that are related to the control of the irradiation system during the irradiation; and
comparing the ascertained dose distribution deposited in the phantom with the calculated expected dose distribution,
wherein the phantom has a motion pattern that differs from the motion signal, and
wherein irradiating the phantom comprises gating, rescanning, tracking, or any combination thereof, the gating comprising activating and deactivating the irradiating using the motion signal, the rescanning comprising building up a total dose in the phantom with multiple successive applications of partial doses at a same site, the tracking comprising deflecting the ion particle beam as a function of the motion signal.

2. The method as defined by claim 1, wherein the phantom is a moving phantom.

3. The method as defined by claim 1, wherein the comparison is made between a nonhomogeneous pattern in the dose distribution deposited in the phantom and an expected nonhomogeneous pattern.

4. The method as defined by claim 1, wherein the parameters used for calculating the expected dose distribution are control parameters that are stored in the irradiation planning data set and include the motion signal.

5. The method as defined by claim 1, wherein the parameters used for calculating the expected dose distribution comprise data that characterize an actual property of a treatment beam during the irradiation.

6. The method as defined by claim 5, wherein the parameters used for calculating the expected dose distribution are used for putting the dose distribution into relation with an imaging data set that is the basis of the irradiation planning data set.

7. The method as defined by claim 5, wherein the parameters used for calculating the expected dose distribution comprise data that characterize a location of the treatment beam, an applied number of particles of the treatment beam during the irradiation, or a combination thereof.

8. The method as defined by claim 1, wherein the motion signal is a virtual motion signal generated internally in a computer unit.

9. The method as defined by claim 1, wherein the motion signal is a motion signal detected by a motion detection device.

10. The method as defined by claim 1, wherein irradiating the phantom comprises irradiating a 3D phantom.

11. The method as defined by claim 10, wherein irradiating the phantom comprises irradiating a plurality of distinguishable regions, the plurality of distinguishable regions comprising materials with a different penetration depth for a particle beam.

12. The method as defined by claim 11, wherein calculating the expected dose distribution comprises taking the constitution of the phantom into account.

13. The method as defined by claim 1, wherein the method is for monitoring the irradiation planning in a particle therapy system, in which with a treatment beam, the dose distribution is depositable in a target object.

14. The method as defined by claim 1, wherein the phantom is constituted anthropomorphically.

15. The method as defined by claim 1, wherein irradiating the phantom comprises gating, rescanning, and tracking.

16. An apparatus for monitoring an irradiation planning, the apparatus comprising:
   a first device, the first device configured for providing an irradiation planning data set that is optimized for irradiating a moving target volume with an ion particle beam generateable by an irradiation system;
   a second device, the second device configured for furnishing a motion signal that simulates a motion of the target volume;
   a phantom operable to detect a dose distribution deposited in the phantom during or after irradiation with the ion particle beam, wherein the phantom has a motion pattern that differs from the motion signal; and
   a computer device configured to:
      calculate an expected dose distribution on the basis of parameters that are related to the control of the irradiation system during the irradiation; and
      compare an ascertained dose distribution deposited in the phantom with the calculated expected dose distribution,
   wherein the phantom is irradiated with the ion particle beam using gating, in which the irradiation controlled by the motion signal is activated and deactivated, rescanning, in which a total dose in the phantom is built up by multiple successive applications of partial doses at a same site, tracking, in which the ion particle beam is deflected as a function of the motion signal, or any combination thereof.

17. The apparatus defined as by claim 16, wherein the apparatus is for monitoring the irradiation planning in a particle therapy system, in which with a treatment beam, the dose distribution is depositable in a target object.

18. An irradiation system comprising:
   an apparatus comprising:
      a first device, the first device configured for providing an irradiation planning data set that is optimized for irradiating a moving target volume with an ion particle beam generateable by an irradiation system;
      a second device, the second device configured for furnishing a motion signal that simulates a motion of the target volume;
      a phantom operable to detect a dose distribution deposited in the phantom during or after irradiation with the ion particle beam, wherein the phantom has a motion pattern that differs from the motion signal; and
      a computer device configured to:
         calculate an expected dose distribution on the basis of parameters that are related to the control of the irradiation system during the irradiation; and
         compare an ascertained dose distribution deposited in the phantom with the calculated expected dose distribution,
   wherein the comparison is made between a nonhomogeneous pattern in the dose distribution deposited in the phantom and an expected nonhomogeneous pattern, and
   wherein the phantom is irradiated with the ion particle beam using gating, in which the irradiation controlled by the motion signal is activated and deactivated, rescanning, in which a total dose in the phantom is built up by multiple successive applications of partial doses at a same site, tracking, in which the ion particle beam is deflected as a function of the motion signal, or any combination thereof.

19. The irradiation system as defined by claim 18, further comprising a particle therapy system.

* * * * *